United States Patent
Kawaguchi et al.

(10) Patent No.: US 8,884,207 B2
(45) Date of Patent: Nov. 11, 2014

(54) PHOTOELECTRIC CONVERSION ELEMENT, DEFECT INSPECTING APPARATUS, AND DEFECT INSPECTING METHOD

(75) Inventors: Hiroshi Kawaguchi, Hitachinaka (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/821,246

(22) PCT Filed: Jul. 26, 2011

(86) PCT No.: PCT/JP2011/066964
§ 371 (c)(1), (2), (4) Date: Mar. 7, 2013

(87) PCT Pub. No.: WO2012/043040
PCT Pub. Date: Apr. 5, 2012

(65) Prior Publication Data
US 2013/0161490 A1    Jun. 27, 2013

(30) Foreign Application Priority Data
Sep. 27, 2010 (JP) ................. 2010-214634

(51) Int. Cl.
| | | |
|---|---|---|
| H01L 27/00 | (2006.01) |
| H04N 3/14 | (2006.01) |
| H04N 5/347 | (2011.01) |
| H04N 5/372 | (2011.01) |
| H01L 27/146 | (2006.01) |
| G01N 21/95 | (2006.01) |
| G01N 21/88 | (2006.01) |

(52) U.S. Cl.
CPC ...... *H01L 27/14601* (2013.01); *G01N 21/8806* (2013.01); *H04N 5/347* (2013.01); *H04N 5/37213* (2013.01); *H04N 5/37206* (2013.01); *G01N 21/9501* (2013.01)
USPC ........................... 250/208.1; 348/295

(58) Field of Classification Search
CPC ... H04N 5/372; H04N 5/347; H04N 5/37206; H04N 5/37213; H04N 5/2722; H04N 5/3725; H04N 5/3728
USPC ............... 250/208.1; 348/295, 303
See application file for complete search history.

(56) References Cited

U.S. PATENT DOCUMENTS

| | | | |
|---|---|---|---|
| 5,402,168 A | 3/1995 | Fouilloy | |
| 6,584,171 B2 * | 6/2003 | Suzuki et al. | 378/98.8 |
| 2011/0221886 A1 | 9/2011 | Nishiyama et al. | |

FOREIGN PATENT DOCUMENTS

| | | |
|---|---|---|
| JP | 1-91577 | 4/1989 |
| JP | 5-167932 | 7/1993 |
| JP | 6-105317 | 4/1994 |

(Continued)

OTHER PUBLICATIONS

Office Action in Japanese Patent Appln. 2010-214634, dispatched Jul. 2, 2013 (in Japanese, 2 pgs.); [including partial English translation, 3 pgs.].

*Primary Examiner* — Thanh Luu
(74) *Attorney, Agent, or Firm* — Antonelli, Terry, Stout & Kraus, LLP.

(57) ABSTRACT

Provided are a photoelectric conversion element, wherein the processing speed can be increased and resolution can be changed without increasing cost, and a defect inspecting apparatus and a defect inspecting method using the photoelectric conversion element. A photoelectric conversion element having a plurality of sensor pixels has a multiplexer and a plurality of horizontal transfer registers. Sensor pixels are divided into a plurality of blocks such that the sensor pixels correspond to each of the horizontal transfer registers. The photoelectric conversion element is configured such that charges of the blocks are read by means of the multiplexer via respective corresponding horizontal transfer registers, and are outputted via the multiplexer.

3 Claims, 6 Drawing Sheets

(56) References Cited

FOREIGN PATENT DOCUMENTS

| JP | 6-319080 | 11/1994 |
| JP | 11-266401 | 9/1999 |
| JP | 2001-53263 | 2/2001 |
| JP | 2004-112304 | 4/2004 |
| JP | 2010-48587 | 3/2010 |

* cited by examiner

PHOTOELECTRIC CONVERSION ELEMENT, DEFECT INSPECTING APPARATUS, AND DEFECT INSPECTING METHOD

TECHNICAL FILED

The present invention relates to a photoelectric conversion element, and a defect inspecting apparatus and a defect inspecting method which employ the photoelectric conversion element. In further detail, the present invention relates to an increase in speed of operation of the photoelectric conversion element, and a defect inspecting apparatus and a defect inspecting method which detect defects (a scratch, a crack, etc.) of an object of the inspection and foreign substances.

BACKGROUND ART

For a photoelectric conversion element, such as a CCD (Charge Coupled Device) and a TDI (Time Delay Integration) which have plural sensor pixels, means for increasing the speed of processing includes a method of raising the clock rate of sensor pixels and a so-called multi output method in which sensor pixels are divided into plural blocks and signals are outputted in parallel for the blocks, for example.

As a conventional technology for methods of increasing the speed of a photoelectric conversion element, Patent Document 1 discloses a method in which the sensor pixels are separated into even-numbered pixels and odd-numbered pixels to output signals and the signals are integrated after A/D conversion.

Examples of means for changing the resolution of a photoelectric conversion element arbitrarily include a method using plural imaging optical systems with different magnifying powers and a method converting the resolution by image processing after obtaining the image data.

DOCUMENTS ON PRIOR ARTS

Patent Document

Patent Document 1: Japanese Unexamined Patent Application Publication No. 5-167932

DISCLOSURE OF THE INVENTION

Problems to be Solved by the Invention

In the method for increasing the speed of a photoelectric conversion element disclosed by Patent Document 1, the processing speed is only doubled because the sensor pixels are divided into only two types, even-numbered pixels and odd-numbered pixels, to output signals.

In the method for raising the clock rate of sensor pixels, the load is doubled as the clock rate is doubled because the photoelectric conversion element is a capacitive load. This may cause insufficiency of the power of a drive circuit and reconsideration and new development of the entire drive circuit will become necessary. Therefore, this method may involve issues such as an increase in period and cost of the development.

Furthermore, in the multi output method, A/D converters are necessary as many as the increased number of the output. Therefore, this method may involve issues such as an increase in cost and an increase in packaging density or area of a mounting board.

The method for using plural imaging optical systems with different magnifying powers to change the resolution of a photoelectric conversion element may involve an issue of an increase in cost. The method for converting the resolution by image processing after obtaining the image data may involve issues such as an increase in cost and an increase in packaging density or area of a mounting board because the number of components necessary for processing mounted on the board and memories is increased.

The object of the present invention is to provide a photoelectric conversion element which can increase the speed of the processing and change the resolution without increasing the cost, and also provide a defect inspecting apparatus and a defect inspecting method which employ the photoelectric conversion element.

Means for Solving the Problem

One aspect of the present invention includes the following features.

A photoelectric conversion element includes a plurality of sensor pixels, a multiplexer, and a plurality of horizontal transfer registers. The sensor pixels are divided into a plurality of blocks such that the sensor pixels correspond to each of the horizontal transfer registers. Charges of the blocks are read by the multiplexer via respective corresponding horizontal transfer registers and are outputted via the multiplexer.

Advantageous Effects of the Invention

According to the present invention, it is possible to provide a photoelectric conversion element which can increase the speed of the processing and change the resolution without increasing the cost of development and manufacturing, and also possible to provide a defect inspecting apparatus and a defect inspecting method which employ the photoelectric conversion element.

DESCRIPTION OF EMBODIMENTS

Figure 1A:
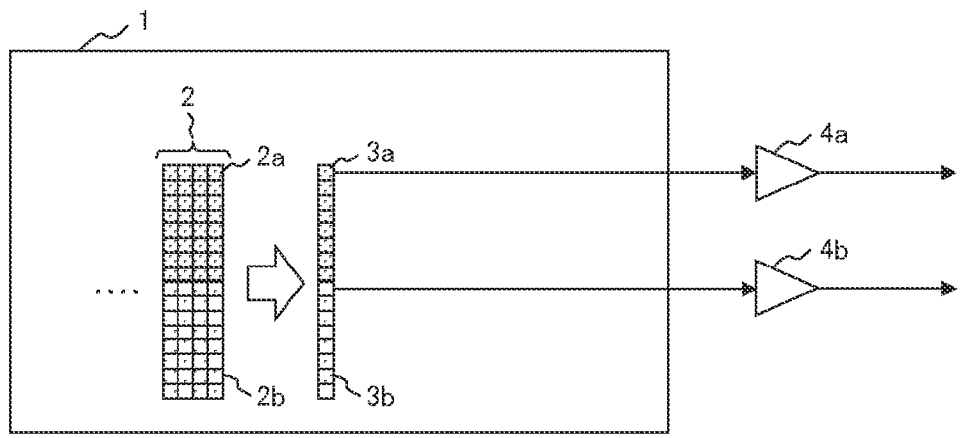
FIG. 1A is a drawing illustrating an example of a conventional photoelectric conversion element.

A photoelectric conversion element according to the present embodiment includes a multiplexer, and divides sensor pixels into plural blocks (N blocks) and outputs charges to the multiplexer for each of the blocks in parallel. In this case, the multiplexer reads and integrates the outputs of N horizontal transfer registers, each of which corresponds to each of the blocks. The multiplexer outputs signals at a speed N times faster than the reading speed. The signals which the multiplexer inputs and outputs are of a charge, a current or a voltage. The following embodiments will be explained on the assumption that the multiplexer mainly inputs and outputs a charge.

The resolution of the photoelectric conversion element can be arbitrarily changed by adding pixels in a pixel direction or a line direction (scanning direction) in the photoelectric conversion element. In the following embodiments, a scanning direction with respect to the sensor pixels in the photoelectric conversion element is called a line direction, and the vertical direction to the line direction is called a pixel direction. The line direction is a direction to which charges are transferred by a vertical transfer register, and the pixel direction is a direction to which charges are transferred by a horizontal transfer register.

According to the photoelectric conversion element according to the present embodiment, it is possible to slow down a clock rate of the horizontal transfer register, that is, a clock rate of the sensor pixels of the photoelectric conversion element, by combining the multiplexer and the plural (N) horizontal transfer registers so that the output speed of the multiplexer is a desired speed. Consequently, it is possible to reduce a noise arising from the high speed drive of the photoelectric conversion element, and it is also possible to improve an SN ratio. Since the clock rate of the sensor pixels is allowed to be slow in the photoelectric conversion element, the speed enhancement can be attained by use of a drive circuit based on the existing technology without developing a new drive circuit, accordingly, suppressing the development cost markedly.

According to the present embodiment, since it is possible to arbitrarily change the resolution of the photoelectric conversion element by adding pixels in the pixel direction or the line direction in the photoelectric conversion element, the defect inspecting apparatus employing the present photoelectric conversion element can set up the optimal resolution in accordance with the size, shape and type of defects to be detected, surface profile of inspection objects, inspection speed, and optical magnification, thereby effectively improving the detection sensitivity. When adding pixels in the line direction, the dynamic range can be improved by enlarging the capacity of the addition register greatly in comparison with registers of the preceding stage (line delay registers), therefore, effectively enabling an advanced identification of the size, shape and type of defects.

Hereinafter, embodiments of the photoelectric conversion element, the defect inspecting apparatus and the defect inspecting method which employ the photoelectric conversion element are explained with reference to the drawings.

The following embodiments will be explained for a TDI (Time Delay Integration) sensor including a vertical transfer register as an example of the photoelectric conversion element. The vertical transfer register functions also as sensor pixels of the photoelectric conversion element. Therefore, the sensor pixels will be called a "sensor pixel/vertical transfer register" in the following embodiments.

The photoelectric conversion element according to the present embodiment has integration function by a multiplexer, pixel-direction adding function of pixels by pixel combining registers, and line-direction adding function of pixels by line delay registers and an addition register. First, the integration function by the multiplexer is explained in comparison with a conventional technology, referring to FIG. 1A and FIG. 1B.

FIG. 1A illustrates an example of a conventional photoelectric conversion element. In the conventional photoelectric conversion element, speed enhancement is attained as follows. Plural sensor pixel/vertical transfer registers 2 in the photoelectric conversion element 1 are divided into blocks. The example of FIG. 1A illustrates the division of two blocks 2a and 2b. Charges of the blocks 2a and 2b are respectively transferred to horizontal transfer registers 3a and 3b, respectively corresponding to the blocks 2a and 2b. The charges of the horizontal transfer registers 3a and 3b are read out for each of the pixels, transformed into voltages by amplifiers (not shown in FIG. 1A), and converted from analog signals to digital signals by A/D converters 4a and 4b, respectively corresponding to the horizontal transfer registers 3a and 3b. The output method described above is generally called a multi-output system and improves the processing speed N times faster, when the number of blocks is N, compared with the case where the division into the blocks is not done.

Figure 1B:
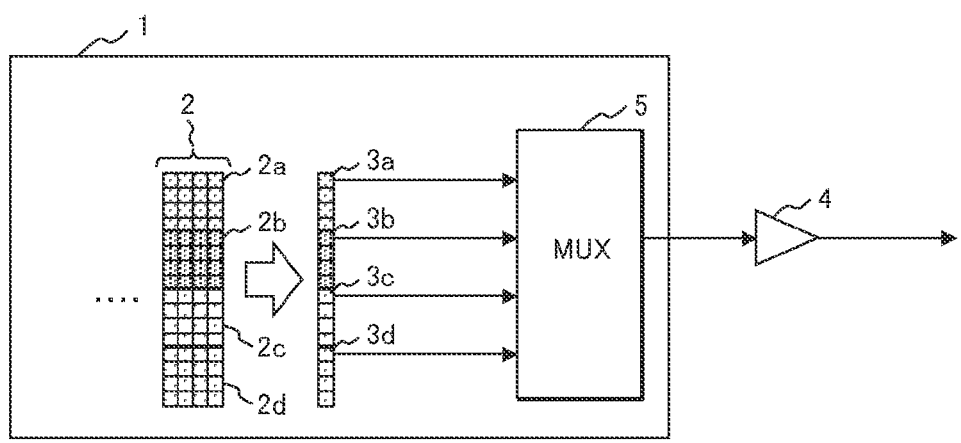
FIG. 1B is a drawing illustrating an integration function in a photoelectric conversion element in accordance with an embodiment of the present invention.

FIG. 1B illustrates an integration function in a photoelectric conversion element according to an embodiment of the present invention. The photoelectric conversion element according to the present embodiment includes a multiplexer connected to a horizontal transfer register and attains speed enhancement as follows.

Plural sensor pixel/vertical transfer registers 2 in a photoelectric conversion element 1 are divided into plural blocks (N blocks). The example of FIG. 1B illustrates the division of four blocks 2a-2d (N=4). Charges of the blocks 2a-2d are respectively transferred to horizontal transfer registers 3a-3d, respectively corresponding to the blocks 2a-2d. The number of the horizontal transfer registers is matched with the number (N) of division of the sensor pixel/vertical transfer registers 2. Charges of the horizontal transfer registers 3a-3d are read out for each of the pixels by the multiplexer 5.

The multiplexer 5 outputs signals at a speed N times faster than a speed of reading out the charges from the horizontal transfer register when the number of the horizontal transfer registers connected to the multiplexer 5 is N, thereby balancing the input speed and the output speed. For example, when the number of the connected horizontal transfer registers is four (N=4) as in the present embodiment, the multiplexer 5 outputs signals at a speed 4 times faster than the speed of reading out the charges from the horizontal transfer register. The output of the multiplexer 5 is converted into voltage by an amplifier (not shown in FIG. 1B), and converted from analog signals to digital signals by an A/D converter 4.

The photoelectric conversion element according to the present embodiment can reduce the number of A/D converters compared with conventional photoelectric conversion elements. Even when the number of blocks is increased, the number of A/D converters are not increased. The clock rate of the sensor pixels may be made slow since it is possible to enhance the speed of processing by increasing the number of blocks. Consequently, it is possible to increase the speed of the photoelectric conversion element by employing a conventional circuit technology without increasing the cost for improving efficiency of a drive circuit. It is possible to reduce a noise arising from the high speed drive by making the clock rate of sensor pixels slow, and it is also possible to improve an SN ratio.

In the embodiment illustrated in FIG. 1B, the TDI (Time Delay Integration) sensor including the vertical transfer register is explained as an example of the photoelectric conversion element. A one-dimensional line scan CCD (Charge Coupled Device) line sensor can be employed as a photoelectric conversion element. Even when the CCD (Charge Coupled Device) line sensor is employed, it is possible to increase the speed of processing without increasing cost, reduce a noise, and improve an SN ratio by combining a multiplexer and plural horizontal transfer registers as described above.

Next, the pixel-direction adding function of pixels by the pixel combining registers and the line-direction adding function of pixels by the line delay registers and the addition register are explained, which are included in the photoelectric conversion element according to the present embodiment, in comparison with a conventional technology with reference to FIGS. 2A-2D.

Figure 2A:
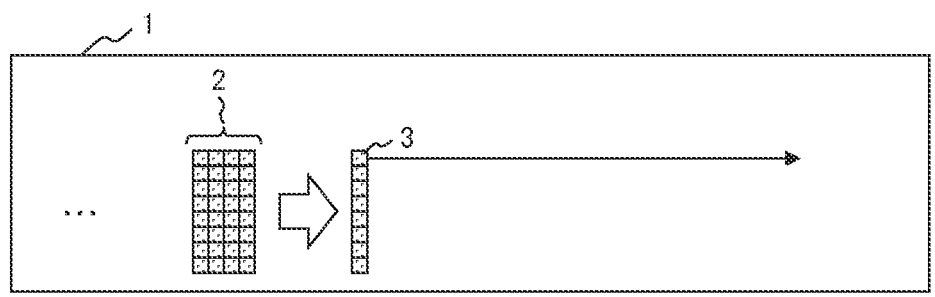
FIG. 2A is a drawing illustrating an example of a charge readout method in a conventional photoelectric conversion element.

FIG. 2A illustrates an example of a charge readout method in a conventional photoelectric conversion element. In a conventional charge readout method, charges are transferred in a lump to the horizontal transfer register 3 from the sensor pixel/vertical transfer register 2 in the photoelectric conversion element 1, and the horizontal transfer register 3 transfers charges to an amplifier (not shown in FIG. 2A) for each of the pixels to convert the charges into voltage. Accordingly, addition of the pixels is performed, when it is needed, by an image processor (not shown in FIG. 2A) in the later stage.

In the photoelectric conversion element according to the present embodiment, the adding functions of pixels are different in the pixel direction and in the line direction. Hereinafter, the adding function of pixels in the pixel direction is explained with reference to FIG. 2B, and the adding function of pixels in the line direction is explained with reference to FIGS. 2C and 2D.

Figure 2B:
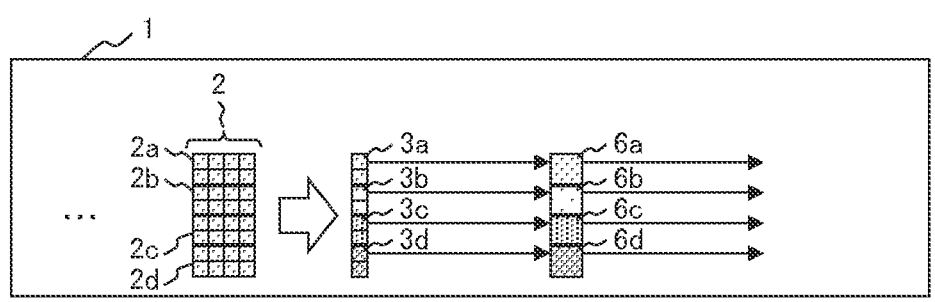
FIG. 2B is a drawing illustrating a pixel-direction adding function of pixels in the photoelectric conversion element in accordance with an embodiment of the present invention.

FIG. 2B illustrates a pixel-direction adding function of pixels in the photoelectric conversion element of the present embodiment. The photoelectric conversion element 1 according to the present embodiment includes a sensor pixel/vertical transfer register 2, horizontal transfer registers 3a, 3b, 3c and 3d, and pixel combining registers 6a, 6b, 6c and 6d. The sensor pixel/vertical transfer register 2 is divided into plural blocks. The example of FIG. 2B illustrates the division of four blocks 2a, 2b, 2c and 2d. The blocks 2a-2d correspond to the horizontal transfer registers 3a-3d, respectively, and the horizontal transfer registers 3a-3d correspond to the pixel combining registers 6a-6d, respectively. The numbers of the blocks, the horizontal transfer registers, and the pixel combining registers, which are four in the present embodiment, are two or more, not limited to four.

The pixel-direction adding function of pixels will be explained in the photoelectric conversion element 1 according to the present embodiment. The sensor pixel/vertical transfer register 2 in the photoelectric conversion element 1 transfers charges in a lump to the horizontal transfer registers 3a-3d. In this case, charges of the blocks 2a-2d are respectively transferred to the horizontal transfer registers 3a-3d respectively corresponding to the blocks 2a-2d. The horizontal transfer registers 3a-3d transfer charges to the respectively corresponding pixel combining registers 6a-6d for each of the pixels. The pixel combining registers 6a-6d add the pixels transferred from the horizontal transfer registers 3a-3d and transfer the charges of the added pixels to an amplifier (not shown in FIG. 2B). The charges transferred to the amplifier are converted into voltage. Here, it is assumed that the capacity of the pixel combining registers 6a-6d are equal to or greater than the capacity for the number of pixels of the horizontal transfer registers 3a-3d, respectively.

In the photoelectric conversion element according to the present embodiment, the photoelectric conversion element 1 can perform the pixel-direction addition of pixels as described above. It is possible to obtain arbitrary resolution when the pixel combining registers 6a-6d, each of which is configured in one stage in the present embodiment, are configured in plural stages.

Figure 3:
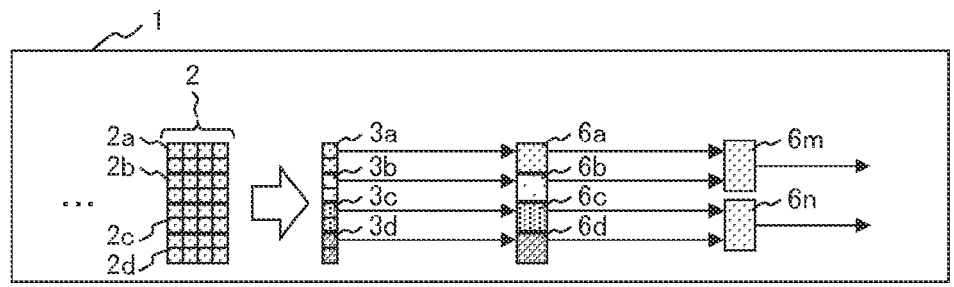
FIG. 3 is a drawing illustrating the photoelectric conversion element in accordance with an embodiment of the present invention, including plural stages of pixel combining registers.

FIG. 3 illustrates a photoelectric conversion element according to an embodiment of the present invention, including plural stages of pixel combining registers. In FIG. 3, the number of the stages of the pixel combining registers is two as an example. The pixel combining registers 6a-6d are provided in the first stage and the pixel combining registers 6m and 6n are provided in the second stage. Pixels transferred to the pixel combining registers 6a and 6b are transferred to the pixel combining register 6m, and pixels transferred to the pixel combining registers 6c and 6d are transferred to the pixel combining register 6n. In this way, it is possible to change the resolution in the pixel direction by changing the size of one pixel with the plural stages of the pixel combining registers.

Figure 2C:
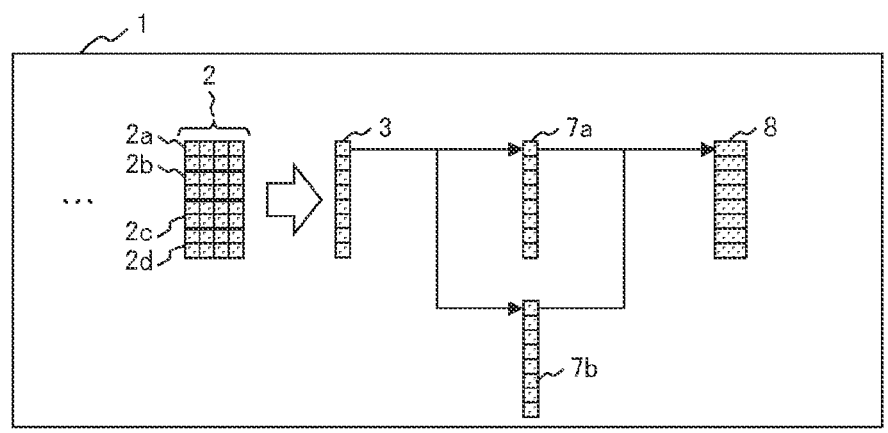
FIG. 2C is a drawing illustrating a line-direction adding function of pixels in the photoelectric conversion element in accordance with an embodiment of the present invention.

FIG. 2C illustrates a line-direction adding function of pixels in the photoelectric conversion element according to the embodiment. The photoelectric conversion element 1 according to the present embodiment includes a sensor pixel/vertical transfer register 2, a horizontal transfer register 3, line delay registers 7a and 7b, and an addition register 8. The sensor pixel/vertical transfer register 2 is divided into plural blocks. The example of FIG. 2C illustrates the division of four blocks 2a, 2b, 2c and 2d. The number of the blocks, which are four in the present embodiment, are two or more, not limited to four.

Charges corresponding to each of line scans are transferred to the line delay registers 7a and 7b for each line of the line scans. That is, charges of the line scans at different time are transferred to the line delay registers 7a and 7b, and the line delay registers 7a and 7b stores the transferred charges. The number of the line delay registers in the photoelectric conversion element 1, which is two in FIG. 2C, may be three or more.

The line-direction adding function of pixels will be explained in the photoelectric conversion element 1 according to the present embodiment. The sensor pixel/vertical transfer register 2 in the photoelectric conversion element 1 transfers charges of the blocks 2a-2d in a lump to the horizontal transfer register 3. The horizontal transfer register 3 transfers charges for each pixel for each line to the line delay registers 7a and 7b corresponding to each of the line scans. The line delay registers 7a and 7b transfer the transferred charges to the addition register 8. The addition register 8 adds the transferred charges and transfers the added charges to an amplifier (not shown in FIG. 2C). The charges transferred to the amplifier are converted into voltage. Here, it is assumed that the capacity of the addition register 8 is equal to or greater than the capacity for the number of pixels of the line delay registers 7a and 7b multiplied by the number of the lines.

In the photoelectric conversion element according to the present embodiment, the photoelectric conversion element 1 can perform the line-direction addition of pixels as described above. In the present embodiment, two line delay registers 7a and 7*b* are provided by assuming two stages of the line delay registers. It is possible to obtain arbitrary resolution by providing two or more stages of the line delay registers and changing the size of one pixel. It may be possible to obtain arbitrary resolution by switching two of the line delay registers 7*a* and 7*b* alternately like a double buffer memory. As described above, it is possible to change the resolution in the line direction in the photoelectric conversion element according to the present embodiment.

Figure 2D:
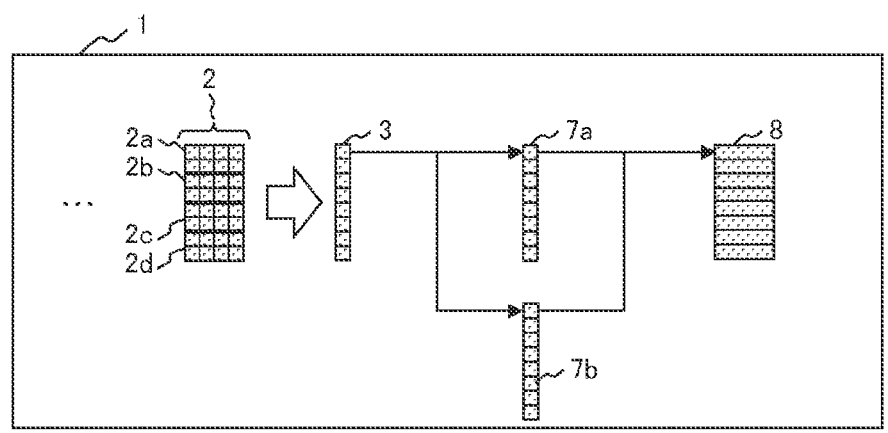
FIG. 2D is a drawing illustrating the photoelectric conversion element in accordance with an embodiment of the present invention, including an addition register having an larger capacity.

FIG. 2D illustrates the photoelectric conversion element according to the embodiment illustrated in FIG. 2C, including an addition register 8 having an larger capacity. When two of the line delay registers 7*a* and 7*b* are utilized like a double buffer memory in the line-direction adding function of pixels illustrated in FIG. 2C, the capacity of the addition register 8 is drastically made larger than the capacity for the number of pixels of the line delay registers 7*a* and 7*b* multiplied by the number of the lines, thereby increasing the full well capacity, as illustrated in FIG. 2D. It is possible to perform any addition by making the full well capacity of the addition register 8 larger than the capacity corresponding to the charges of the line delay registers 7*a* and 7*b*. Accordingly, it is also possible to increase the dynamic range.

As a photoelectric conversion element, a one-dimensional line scan CCD (Charge Coupled Device) line sensor can be employed, while a TDI (Time Delay Integration) sensor with the vertical transfer register is exemplified in the embodiment illustrated in FIG. 2B-FIG. 2D. Even when a CCD (Charge Coupled Device) line sensor is employed, it is possible to increase the speed of processing and change the resolution without increasing cost by combining the multiplexer and plural horizontal transfer registers as described above. It is also possible to reduce a noise and improve an SN ratio.

In the above, the explanations have been made separately for three functions of the photoelectric conversion element: the integration function by the multiplexer, the pixel-direction adding function by the pixel combining registers, and the line-direction adding function by the line delay registers and the addition register. It is possible to combine these three functions.

Figure 4:
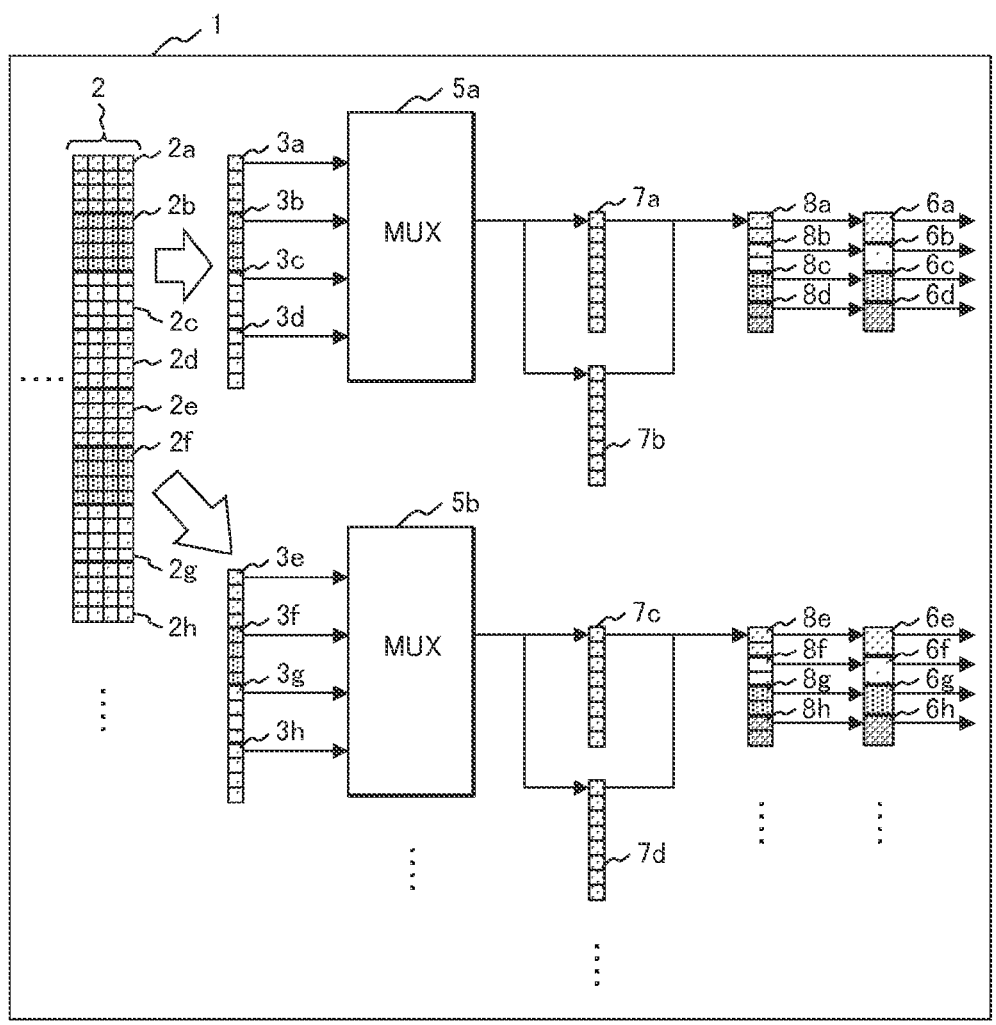
FIG. 4 is a drawing illustrating the photoelectric conversion element in accordance with an embodiment of the present invention, including a combination of the integration function, the pixel-direction adding function, and the line-direction adding function.

FIG. 4 illustrates a photoelectric conversion element according to an embodiment of the present invention, including a combination of three functions of the integration function, the pixel-direction adding function, and the line-direction adding function. The photoelectric conversion element 1 according to the present embodiment including a sensor pixel/vertical transfer register 2, horizontal transfer registers 3*a*-3*h*, multiplexers 5*a* and 5*b*, line delay registers 7*a*-7*d*, addition registers 8*a*-8*h*, and pixel combining registers 6*a*-6*h*. The sensor pixel/vertical transfer register 2 is divided into plural blocks. The example of FIG. 4 illustrates the division of eight blocks 2*a*-2*h*. The blocks 2*a*-2*h* correspond to the horizontal transfer registers 3*a*-3*h*, respectively. The addition registers 8*a*-8*h* correspond to the pixel combining registers 6*a*-6*h*, respectively.

The numbers of the blocks, the horizontal transfer registers, the addition registers, and the pixel combining registers, which are eight in the present embodiment, are two or more, not limited to eight. The number of the line delay registers is also not limited to the number illustrated in FIG. 4.

The number of the multiplexers may be one or more. Each multiplexer reads out signals from the plural horizontal transfer registers and outputs the read signals one by one.

Charges of the blocks 2*a*-2*h*, into which the sensor pixel/vertical transfer register 2 is divided, are transferred to the horizontal transfer registers 3*a*-3*h* corresponding to the blocks 2*a*-2*h*, respectively. Charges of the horizontal transfer registers 3*a*-3*h* are read out by the multiplexers 5*a* and 5*b* for each of the pixels. The multiplexer 5*a* reads out charges of the horizontal transfer registers 3*a*-3*d*, and the multiplexer 5*b* reads out charges of the horizontal transfer registers 3*e*-3*h*, respectively.

The multiplexer 5*a* outputs signals at a speed N times faster than a speed of reading out the charges from the horizontal transfer register when the number of the horizontal transfer registers connected to the multiplexer 5 is N, thereby balancing the input speed and the output speed. For example, when the number of the connected horizontal transfer registers is four (N=4) as illustrated in FIG. 4, the multiplexer 5*a* outputs signals at a speed 4 times faster than the speed of reading out the charges from the horizontal transfer register. The multiplexer 5*b* also outputs signals at the speed determined by the same way as in the multiplexer 5*a*. The outputs of the multiplexers 5*a* and 5*b* are transferred to the line delay registers 7*a*-7*d* corresponding to the multiplexers 5*a* and 5*b* for each line of the line scans. In FIG. 4, the line delay registers 7*a* and 7*b* correspond to the multiplexer 5*a*, and the line delay registers 7*c* and 7*d* correspond to the multiplexer 5*b*. The line delay registers 7*a* and 7*b* receives the charges of the line scans at different times. The line delay registers 7*c* and 7*d* also receives the charges of the line scans at different times. The line delay registers 7*a*-7*d* store the transferred charges.

The line delay registers 7*a* and 7*b* transfer the transferred charges to the addition registers 8*a*-8*d*, and the line delay registers 7*c* and 7*d* transfer the transferred charges to the addition registers 8*e*-8*h*.

The addition registers 8*a*-8*h* transfer charges for each of the pixels to the corresponding pixel combining registers 6*a*-6*h*, respectively, and thereby, perform addition of pixels for the number of pixels which the addition registers 8*a*-8*h* transfer.

The pixel combining registers 6*a*-6*h* add the pixels transferred from the addition registers 8*a*-8*h* and transfer the charges of the added pixels to an amplifier (not shown in). The charges transferred to the amplifier are converted into voltage, and the analog signal voltage is converted into a digital signal by an A/D converter (not shown in FIG. 4).

It is not always necessary to use together three functions of the integration function by the multiplexer, the pixel-direction adding function by the pixel combining registers, and the line-direction adding function by the line delay registers and the addition register. It is possible to select and combine only necessary functions to use among these three functions in the photoelectric conversion element according to the present embodiment.

By the above described approach, it is possible to realize the photoelectric conversion element which has three functions: the integration function by the multiplexer, the pixel-direction adding function by the pixel combining registers, and the line-direction adding function by the line delay registers and the addition register.

Accordingly, the photoelectric conversion element according to the present embodiment can reduce the number of A/D converters compared with conventional photoelectric conversion elements owing to the integration function by the multiplexer. Even when the number of blocks is increased, the number of A/D converters are not increased. The clock rate of the sensor pixels may be made slow since it is possible to enhance the speed of processing by increasing the number of blocks. Consequently, it is possible to increase the speed of the photoelectric conversion element by employing a conventional circuit technology without increasing the cost for improving efficiency of a drive circuit. It is possible to reduce a noise arising from the high speed drive by making the clock rate of sensor pixels slow, and it is also possible to improve an SN ratio.

Furthermore, it is possible to perform addition of the pixels in the line direction in the photoelectric conversion element 1 and to change the resolution in the line direction by setting the capacity of the addition register to be equal to or larger than the capacity for the number of pixels of the line delay registers multiplied by the number of lines. It is possible to obtain arbitrary resolution when the line delay registers, which are configured in two stages in the present embodiment, are configured in two or more stages.

It may be possible to obtain arbitrary resolution by using the two line delay registers like a double buffer memory. At this time, as illustrated in FIG. 2D, the capacity of the addition register is drastically made larger than the capacity for the number of pixels of the line delay registers multiplied by the number of the lines, and thereby, it is possible to perform any addition and increase the dynamic range.

Furthermore, it is possible to perform addition of pixels in the photoelectric conversion element 1 and change the resolution in the pixel direction by setting the capacity of the pixel combining registers to be equal to or greater than the capacity for the number of pixels of the addition register. It is possible to obtain arbitrary resolution when the pixel combining registers, which are configured in one stage in the embodiment illustrated in FIG. 4, are configured in plural stages as illustrated in FIG. 3. As a photoelectric conversion element, a one-dimensional line scan CCD (Charge Coupled Device) line sensor can be employed, while a TDI (Time Delay Integration) sensor with the vertical transfer register is exemplified in the embodiment illustrated in FIG. 4.

Figure 5:
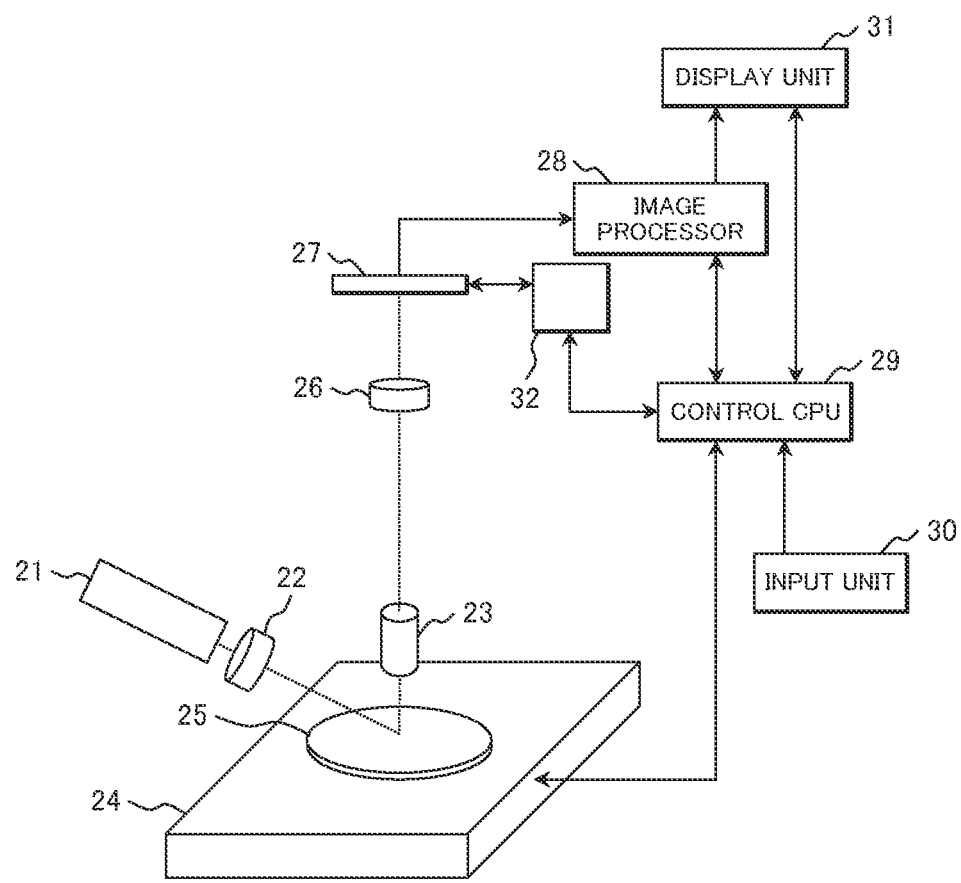
FIG. 5 is a drawing illustrating a defect inspecting apparatus in accordance with an embodiment of the present invention, including a photoelectric conversion element of the present invention.

FIG. 5 illustrates a defect inspecting apparatus according to an embodiment of the present invention, including a photoelectric conversion element of the present invention. The defect inspecting apparatus according to the present embodiment is an optical wafer inspecting apparatus and detects defects (a scratch, a crack, etc.) of a wafer, an object of inspection, and foreign substances.

As illustrated in FIG. 5, the defect inspecting apparatus according to the embodiment includes a light source 21 which emits an illumination light, a beam expander 22, a stage 24 on which a sample 25 is mounted as an object of inspection, an objective lens 23, an imaging lens 26, and an image sensor 27 as a detector. The defect inspecting apparatus further includes a display unit 31, an input unit 30, an image processor 28, an element configuration controller 32 which controls a photoelectric conversion element, and a control CPU 29.

The image sensor 27 includes a photoelectric conversion element according to an embodiment of the present invention. That is, the photoelectric conversion element has three functions of the integration function by a multiplexer, the pixel-direction adding function by a pixel combining registers, and the line-direction adding function by a line delay registers and an addition register. It is possible to select and combine only necessary functions to use among these three functions in the defect inspecting apparatus of the present embodiment.

The sample 25 mounted on the stage 24 is irradiated with an illumination light from the light source 21 through the beam expander 22. A reflected light from the sample 25 is detected by the image sensor 27 through the objective lens 23, the imaging lens 26, etc.

The display unit 31 displays results of the image processing and the configuration information of the photoelectric conversion element. The control CPU 29 controls information inputted by the input unit 30 and also controls data and information of the image processor 28, the image sensor 27, the stage 24, and the element configuration controller 32.

The element configuration controller 32 performs switching control of the combination of three functions of the photoelectric conversion element, which are the integration function by the multiplexer, the pixel-direction adding function by the pixel combining registers, and the line-direction adding function by the line delay registers and the addition register, according to the size, shape and type of defects to be detected, the surface profile of an object of inspection (the sample 25), inspection speed, and optical magnification. The switching control of these three functions is performed based on a setup of the photoelectric conversion element which a user has inputted. The user specifies the setup of control of the photoelectric conversion element via the input unit 30, such as whether the integration function is necessary or not, whether to change the resolution or not, and the direction of adding pixels (pixel direction, line direction, or both directions) when the resolution is changed. The element configuration controller 32 can control the configuration of the photoelectric conversion element to any resolution and sensitivity.

Figure 6:
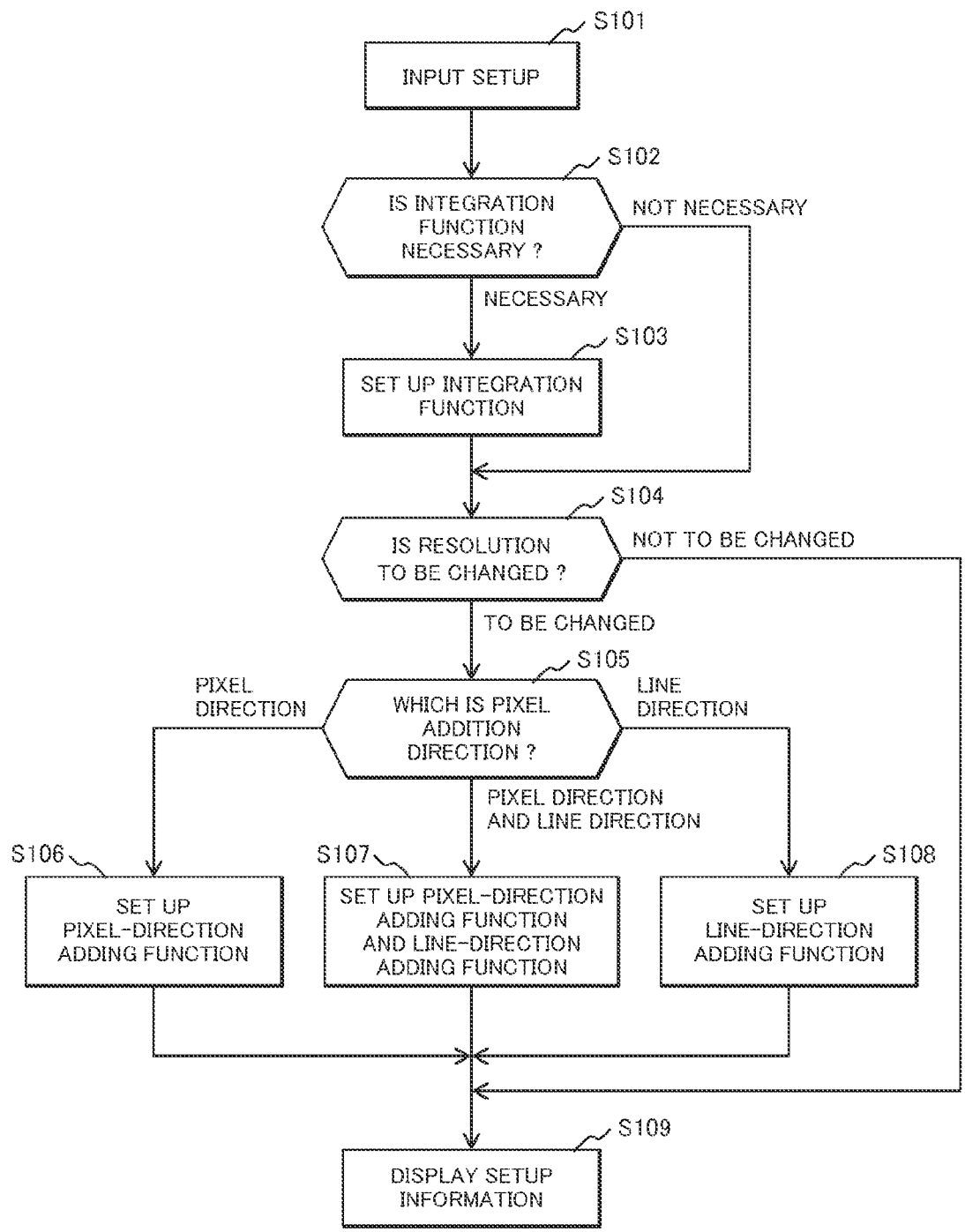
FIG. 6 is a flow chart illustrating steps for setting up the control processing executed by an element configuration controller.

FIG. 6 is a flow chart illustrating steps for setting up the control processing executed by the element configuration controller 32. The steps for setting up the control processing of the element configuration controller 32 are as follows.

At Step 101, a setup of the photoelectric conversion element is inputted. The user specifies the setup of the photoelectric conversion element via the input unit 30, such as whether the integration function is necessary or not, whether to change the resolution or not, and the direction of adding pixels (pixel direction, line direction, or both directions) to change the resolution when the resolution is changed.

At Step 102, it is determined whether the integration function is necessary or not according to the inputted setup. The flow proceeds to Step 103 when necessary, and the flow proceeds to Step 104 when not necessary.

At Step 103, the integration function by the multiplexer is set up according to the inputted setup.

At Step 104, it is determined whether to change the resolution according to the inputted setup. The flow proceeds to Step 105 when changing the resolution, and the flow proceeds to Step 109 when not changing.

At Step 105, the direction of adding pixels is selected according to the inputted setup.

When the addition is performed in the pixel direction, the flow proceeds to Step 106 and the pixel-direction adding function by the pixel combining registers is set up. Subsequently, the flow proceeds to Step 109.

When the addition is performed in the pixel direction and the line direction, the flow proceeds to Step 107 and the pixel-direction adding function by the pixel combining registers and the line-direction adding function by the line delay registers and the addition register are set up. Subsequently, the flow proceeds to Step 109.

When the addition is performed in the line direction, the flow proceeds to Step 108 and the line-direction adding function by the line delay registers and the addition register is set up. Subsequently, the flow proceeds to Step 109.

At Step 109, the setup information (the setup values and the normality or abnormality of the termination of the setup, for example) is displayed on the display unit 31. When the setup of the element configuration controller 32 is normal, the user shifts to other operations, such as defect inspection. When the setup is abnormal, the user specifies the setup again, returning to Step 101.

The defect inspecting apparatus according to the present embodiment can be set up at the optimal resolution with respect to the size, shape and type of defects to be detected, the surface profile of an object of inspection, inspection speed, and optical magnification based on such a configuration described above. Accordingly, as for the hardware except for the photoelectric conversion element, any change from a conventional defect inspecting apparatus is unnecessary, and it is possible to easily change and adjust the resolution and sensitivity of the device. Furthermore, the dynamic range is increased and it is possible to highly identify the size, shape and type of defects as the photoelectric conversion element employs the addition register with the capacity drastically larger than the capacity for the number of pixels of the line delay registers multiplied by the number of the lines.

In the present embodiment, the light source 21 is arranged at a slanting position from the stage 24 to provide an oblique illumination, and the image sensor 27 is arranged above the stage 24 to detect the reflected light upward, as illustrated in FIG. 5. The arrangements of the light source 21 and the image sensor 27 are not limited to the places in the embodiment. It is needless to say that the light source 21 and the image sensor 27 may be arranged at any places as long as the illumination light from the light source 21 can irradiate the sample 25 mounted on the stage 24 and the image sensor 27 can detect the reflected light from the sample 25.

EXPLANATION OF REFERENCE CHARACTERS

1—photoelectric conversion element
2—vertical transfer register
2a, 2b, 2c, 2d, 2e, 2f, 2g, 2h—block
3, 3a, 3b, 3c, 3d, 3e, 3f, 3g, 3h—horizontal transfer register
4, 4a, 4b—A/D converter
5, 5a, 5b—multiplexer
6a, 6b, 6c, 6d, 6e, 6f, 6g, 6h, 6m, 6n—pixel combining register
7a, 7b, 7c, 7d—line delay register
8, 8a, 8b, 8c, 8d, 8e, 8f, 8g, 8h—addition register
21—light source
22—beam expander
23—objective lens
24—stage
25—sample
26—imaging lens
27—image sensor
28—image processor
29—control CPU
30—input unit
31—display unit
32—element configuration controller

What is claimed is:

1. A photoelectric conversion element comprising:
a plurality of sensor pixels;
a multiplexer;
a plurality of horizontal transfer registers;
a plurality of line delay registers configured to store charges for each corresponding line of line scans;
a plurality of addition registers, wherein the addition registers are configured to add signals transferred from the line delay registers; and
a plurality of pixel combining registers corresponding to each of the addition registers, wherein the pixel combining registers are configured to add pixels transferred from the addition registers,
wherein the sensor pixels are divided into a plurality of blocks such that the sensor pixels correspond to each of the horizontal transfer registers,
wherein charges of the blocks of the sensor pixels are transferred to respective corresponding horizontal transfer registers,
wherein the multiplexer reads signals from the horizontal transfer registers and outputs the signals,
wherein each of the line delay registers stores the signals outputted by the multiplexer for each corresponding line scan,
wherein the signals are transferred from the line delay registers to the addition registers, and
wherein the signals of the addition registers are transferred to the respective corresponding pixel combining registers.

2. A defect inspecting apparatus comprising:
a detector including a photoelectric conversion element; and
an element configuration controller,
wherein the apparatus inspects defects of a sample by detecting a reflected light from the sample using the detector,
wherein the photoelectric conversion element comprises a plurality of sensor pixels divided into a plurality of blocks; a plurality of horizontal transfer registers configured to input charges from respective corresponding blocks; a multiplexer including an integration function to read signals from the horizontal transfer registers and output the signals; a plurality of line delay registers configured to store the signals outputted by the multiplexer for each corresponding line of line scans; a plurality of addition registers configured to input the signals from the line delay registers; and a plurality of pixel combining registers including a pixel-direction adding function to input the signals of the respective corresponding addition registers and add pixels, and
wherein the element configuration controller performs, according to a specified setup, switching control of the integration function, the pixel-direction adding function, and a line-direction adding function to add pixels using the line delay registers and the addition registers.

3. A defect inspecting method for inspecting defects of a sample by detecting a reflected light from the sample using a detector including a photoelectric conversion element, the defect inspecting method comprising the steps of:
inputting a setup for controlling the photoelectric conversion element including a multiplexer, horizontal transfer registers, pixel combining registers, line delay registers, and an addition register;
setting up an integration function by the photoelectric conversion element according to the setup, the integration function being a function that the multiplexer reads signals from the horizontal transfer registers respectively corresponding to sensor pixels divided into a plurality of blocks and outputs the signals; and
setting up at least one of functions by the photoelectric conversion element according to the setup, the functions including a pixel-direction adding function to transfer charges from the sensor pixels to the horizontal transfer registers and transfer the charges from the horizontal transfer registers to the pixel combining registers and a line-direction adding function to transfer charges from the sensor pixels to the horizontal transfer registers, transfer the charges from the horizontal transfer registers to the line delay registers, and transfer the charges from the line delay registers to the addition register.

* * * * *